United States Patent [19]
Wallace

[11] Patent Number: 5,304,216
[45] Date of Patent: Apr. 19, 1994

[54] ICE PACK APPARATUS

[76] Inventor: Robert B. Wallace, 4760 College Ave., San Diego, Calif. 92115

[21] Appl. No.: 9,149

[22] Filed: Jan. 26, 1993

[51] Int. Cl.5 .................................................. A61F 7/00
[52] U.S. Cl. ..................................... 607/112; 607/108; 62/530
[58] Field of Search ............... 128/399, 402, 403, 374, 128/380; 62/530; 602/2

[56] References Cited

U.S. PATENT DOCUMENTS

| | | | |
|---|---|---|---|
| 3,506,013 | 4/1970 | Zdenek | 128/402 |
| 3,889,684 | 6/1975 | Lebold | 128/402 |
| 4,055,188 | 10/1977 | Pelton | 128/402 |
| 4,344,303 | 8/1982 | Kelley, Jr. | 128/402 |
| 4,576,169 | 3/1986 | Williams | 128/402 |
| 4,628,932 | 12/1986 | Tampa | 128/402 |
| 4,676,247 | 6/1987 | Van Cleve | 128/402 |
| 4,981,135 | 1/1991 | Hardy | 128/402 |

Primary Examiner—Mark S. Graham
Attorney, Agent, or Firm—Leon Gilden

[57] ABSTRACT

An ice pack includes a flexible base web, having a polymeric foam web connected to a bottom surface of the base web for frictional engagement with a skin portion of an individual, with at least one refrigerant housing mounted to a top surface of the base web positioned over the foam web. Fastener structure is arranged to opposed ends of the base web to secure about an individual. The base web structure is formed of various lengths to accommodate various appendage portions of an individual's body.

3 Claims, 4 Drawing Sheets

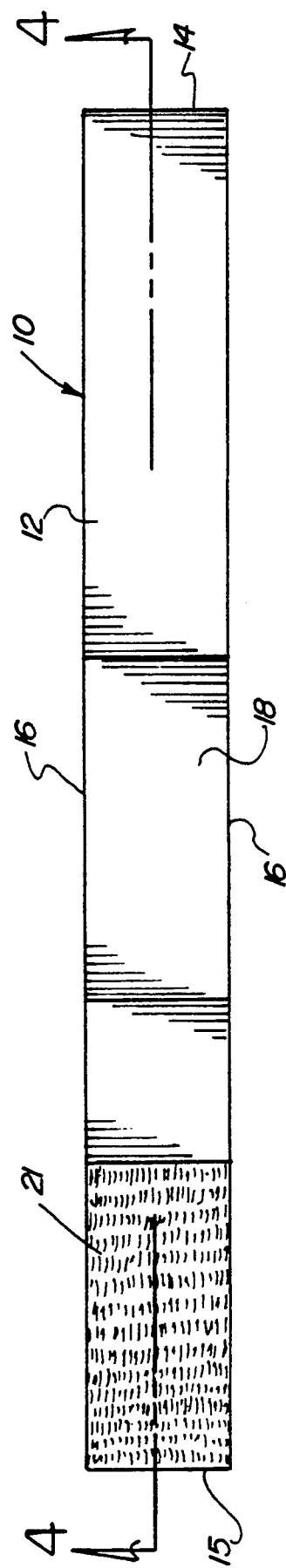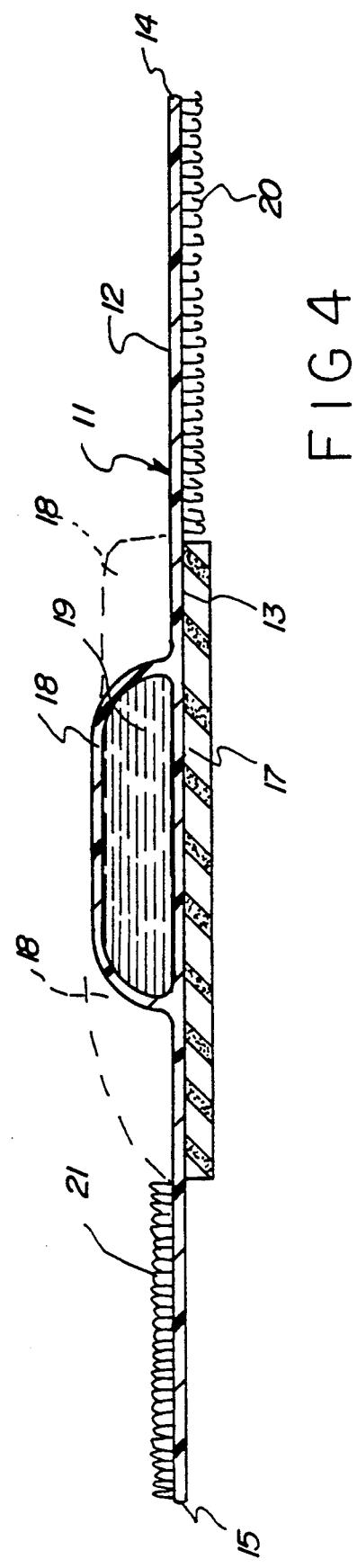

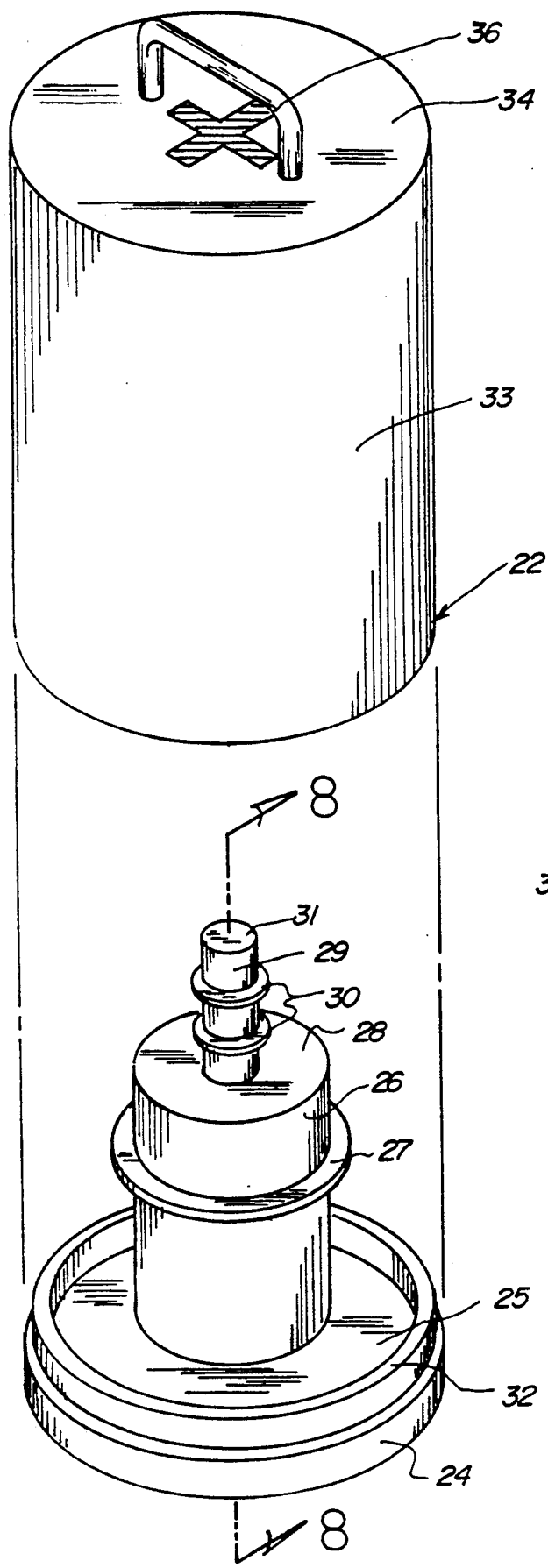
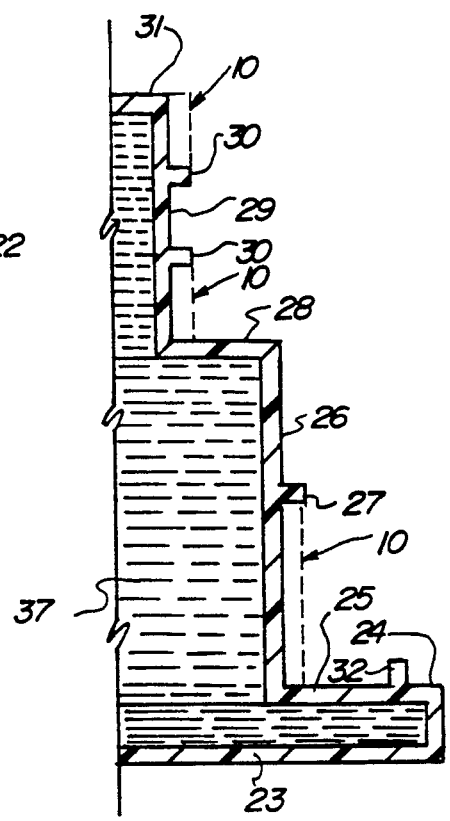
FIG 7
FIG 8

ICE PACK APPARATUS

BACKGROUND OF THE INVENTION

1. Field of the Invention

The field of invention relates to ice pack apparatus, and more particularly pertains to a new and improved ice pack apparatus wherein the same is arranged for securement about an individual.

2. Description of the Prior Art

Various ice pack wraps, such as indicated in U.S. Pat. Nos. 5,000,176; 4,311,022; and 4,971,041 are available in the prior art.

The instant invention sets forth an improvement over the prior art by including a polymeric foam web mounted to a flexible web to provide for enhanced frictional engagement of the wrapping web relative to an individual in use and in this respect, the present invention substantially fulfills this need.

SUMMARY OF THE INVENTION

In view of the foregoing disadvantages inherent in the known types of ice pack apparatus now present in the prior art, the present invention provides an ice pack apparatus wherein the same is arranged for the securement about an individual. As such, the general purpose of the present invention, which will be described subsequently in greater detail, is to provide a new and improved ice pack apparatus which has all the advantages of the prior art ice pack apparatus and none of the disadvantages.

To attain this, the present invention provides an ice pack including a flexible base web, having a polymeric foam web connected to a bottom surface of the base web for frictional engagement with a skin portion of an individual, with at least one refrigerant housing mounted to a top surface of the base web positioned over the foam web. Fastener structure is arranged to opposed ends of the base web to secure about an individual. The base web structure is formed of various lengths to accommodate various appendage portions of an individual's body.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved ice pack apparatus which has all the advantages of the prior art ice pack apparatus and none of the disadvantages.

It is another object of the present invention to provide a new and improved ice pack apparatus which may be easily and efficiently manufactured and marketed.

It is a further object of the present invention to provide a new and improved ice pack apparatus which is of a durable and reliable construction.

An even further object of the present invention is to provide a new and improved ice pack apparatus which is susceptible of a low cost of manufacture with regard to both materials and labor, and which accordingly is then susceptible of low prices of sale to the consuming public, thereby making such ice pack apparatus economically available to the buying public.

Still yet another object of the present invention is to provide a new and improved ice pack apparatus which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an orthographic top view of the invention.

FIG. 4 is an orthographic side view of the invention.

FIG. 7 is an isometric illustration of a support housing for supporting a plurality of web members thereabout for positioning within the refrigerant compartment.

FIG. 8 is an orthographic view, taken along the lines 8—8 of FIG. 7 in the direction indicated by the arrows.

DESCRIPTION OF THE PREFERRED EMBODIMENT

Figure 1:
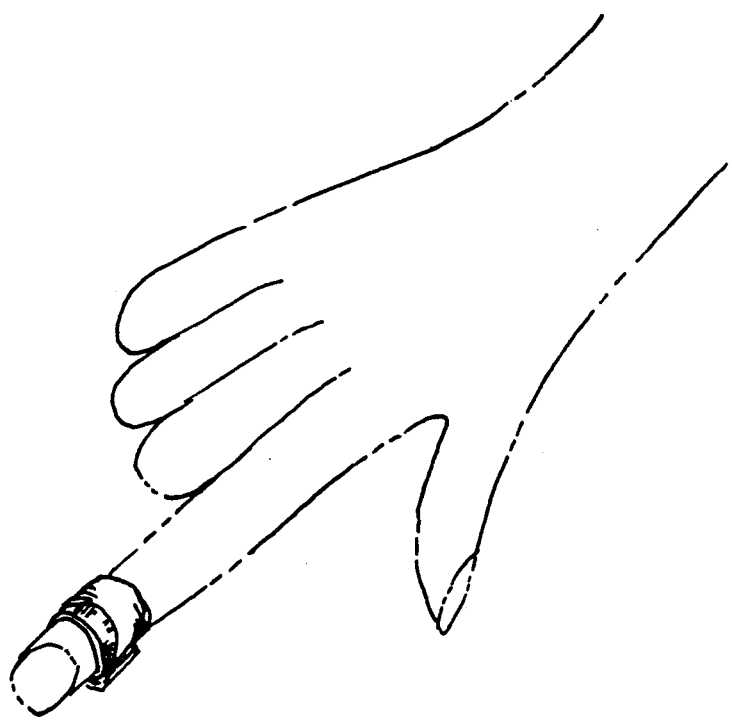
FIG. 1 is an isometric illustration of the invention wrapped around an individual's finger.

With reference now to the drawings, and in particular to FIGS. 1 to 8 thereof, a new and improved ice pack apparatus embodying the principles and concepts of the present invention and generally designated by the reference numerals 11–37 will be described.

Figure 2:
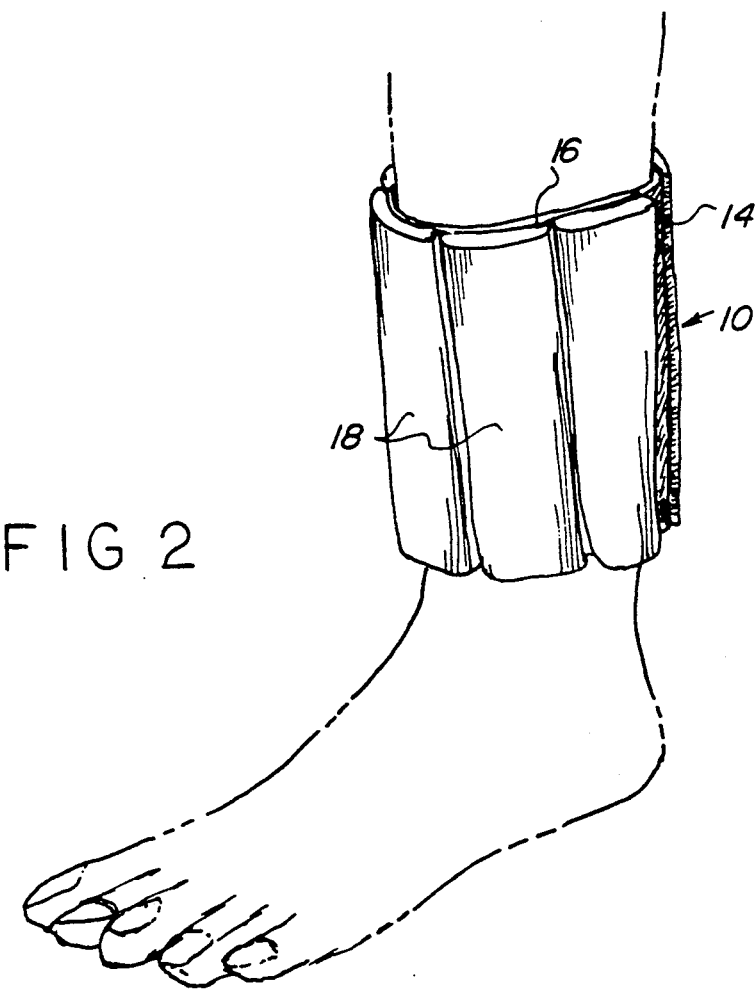
FIG. 2 is an isometric illustration of the invention wrapped around a leg portion of an individual.
Figure 5:
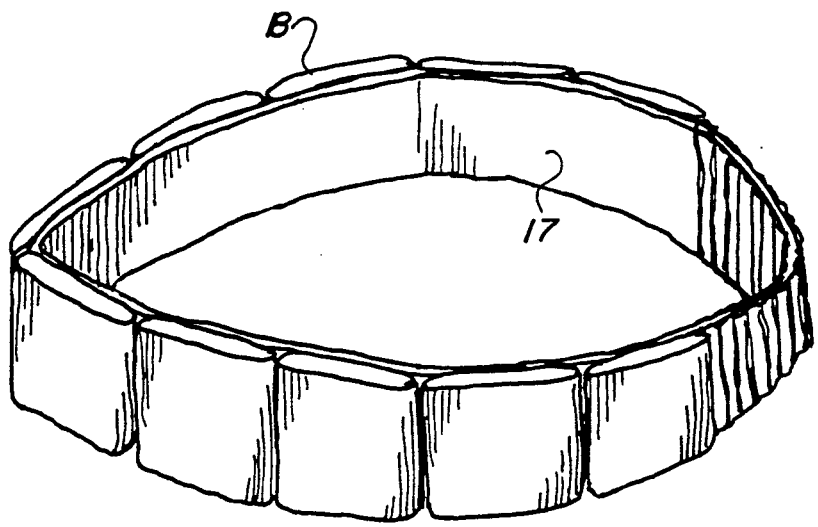
FIG. 5 and FIG. 6 are isometric views of the ice pack wrap employing a plurality of gelatin housings mounted about the base web.
Figure 6:
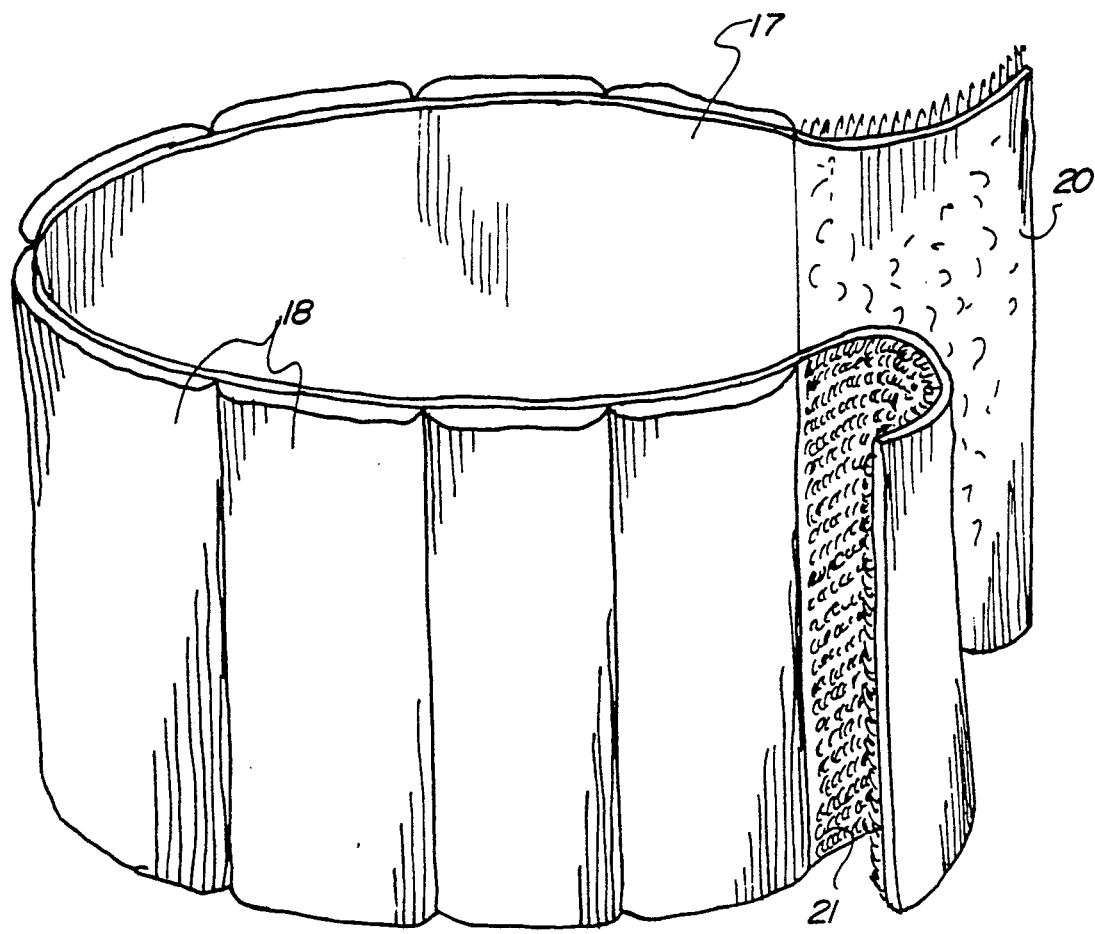

More specifically, the ice pack apparatus of the invention essentially comprises a wrap 10, wherein the wrap 10 may be of various lengths to accommodate various body appendages such as a finger, as illustrated in FIG. 1, or an ankle portion, as illustrated in FIG. 2. The wrap includes (see FIGS. 2–4) a flexible base web 11, having a top surface 12 spaced from a bottom surface 13, with a first end 14 spaced from a second end 15 and spaced parallel sides 16. A polymeric foam web 17 is mounted medially of the bottom surface 13 spaced from the first and second ends 14 and 15 and coextensive between the sides 16. A flexible refrigerant housing 18 is mounted to the top surface positioned over the base web, wherein a plurality of such refrigerant housings 18 may be employed, as indicated in FIG. 2 for example, that are coextensively oriented relative to the front web 17. A refrigerant gel 19 is contained within each refrigerant housing 18. A first hook and loop fastener patch 20 extends from the foam web 17 to the first end 14 onto the bottom surface 13. A second hook and loop fastener patch 21 secured to the first hook and loop fastener patch 20 are wrapped around an individual's appendage and mounted to the top surface 12 between the foam web 17 and the second end 15. The foam web thereby provides for unobstructed conduit for a refrigerant directed to an individual's skin portion, as well as providing enhanced traction to the individual's skin to provide for limited slippage relative to the skin in use.

Reference to FIGS. 7 and 8 indicates the use of a support housing 22 arranged to receive a plurality of therapeutic wraps 10 permitting insertion of the wraps about the support housing 22 within a freezing compartment for cooling of the gel 19. The housing 22 includes a first floor 23, having a first cylindrical side wall 24 of a first diameter. A second floor 25 spaced above and parallel to the first floor extends from the first side wall 24 to a second cylindrical side wall 26, having a second diameter less than the first diameter. The second cylindrical side wall 26 extends to a third floor 28, with the second side wall 26 orthogonally oriented between the second floor and the third floor 28. The third floor 28 is parallel to the first and second floors and extends from the second side wall to a third cylindrical side wall 29, having a third diameter less than the second diameter, that in turn is orthogonally oriented relative to the third floor and extends to a top wall 31. The second side wall 26 includes a first annular rib 27, with the third side wall 29 having at least one, and typically a plurality of, third parallel annular ribs 30. In this manner, positioned between adjacent ribs and between one of the ribs at an associated adjacent floor, a therapeutic wrap is arranged for positioning and mounting. In this manner, the wrap is in an extended orientation for ease of cooling of the gel 19 within each wrap. Within the support housing 22 is a sealed cavity, with the sealed cavity including a further refrigerant gel 37 coextensive therethrough. In this manner, as the further gel 37 is chilled, the support housing 22 permits ease of transport of the wrap structure 10, as well as the housing, to a remote orientation for use and storage, as the further refrigerant gel 37 within the support housing 22 maintains the refrigerant gel 19 within each wrap 10 at a desired temperature. A cylindrical lid is provided, having a cylindrical side wall 33 of a predetermined height substantially equal to the predetermined height extending from the second floor 25 to the top wall 31. Further, a second floor rib 32 maintains the cylindrical lid side wall 33 between the second floor rib 32 and the first side wall 24. The lid includes a lid top wall 34, with the lid top wall 34 including a handle 36 for ease of manipulation of the lid, as well as sealingly enclosing the wrap structure within the lid for maintaining cooling temperatures relative to each wrap secured to the housing structure 22.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An ice pack and housing apparatus, comprising, at least one therapeutic wrap, having a flexible base web, the base web including a top surface spaced from a bottom surface, a first end spaced from a second end, and spaced side walls, and a polymeric foam web mounted coextensively between the side walls and spaced from the first end and the second end, with the foam web mounted to the bottom surface, and at least one flexible refrigerant housing mounted to the top surface positioned over the foam web, the refrigerant housing including a refrigerant gel therewithin, and a first hook and loop fastener patch mounted to the base web, and a second hook and loop fastener patch mounted to the base web, with the first fastener patch and the second fastener patch arranged for securement relative to one another about an individual, and the first hook and loop fastener patch is mounted to the bottom surface between the foam web and the first end coextensive therebetween, and the second hook and loop fastener patch arranged coextensively between the foam web and the second end and mounted to the top surface, and a support housing, the support housing including a first floor, and a first side wall mounted about the first floor, and second floor positioned above the first floor in a parallel relationship, and a second cylindrical side wall mounted to the second floor extending from the second floor, wherein the second side wall is defined by a second diameter, the first side wall defined by a first diameter, wherein the second diameter is less than the first diameter, and the first side wall is orthogonally oriented relative to the second floor, and the first side wall extends to a third floor, wherein the third floor is parallel to the second floor, and a third side wall orthogonally mounted to the third side wall, wherein the third side wall is defined by a third diameter less than the second diameter and extends orthogonally between the third floor and a top wall, with the top wall oriented parallel to the third floor, and the top wall is spaced from the second floor a predetermined height, and a lid, the lid having a lid side wall, the lid side wall having a lid height equal to the predetermined height, and a lid top wall arranged for abutment with the top wall, wherein the lid is mounted upon the second floor.

2. An apparatus as set forth in claim 1 including a second floor annular rib, wherein the lid is arranged for positioning on the second floor between the second floor annular rib and the first side wall, and the second wall having a first annular rib, and the third wall having at least one third wall annular rib, wherein said therapy wrap is arranged for mounting about said second side wall and said third side wall in engagement with one of said ribs.

3. An apparatus as set forth in claim 2 wherein the support housing includes an enclosed housing cavity extending from the first side to the top wall, and the housing cavity having a further refrigerant gel coextensively directed therethroughout.

* * * * *